United States Patent [19]

Debono

[11] 4,293,489

[45] Oct. 6, 1981

[54] DERIVATIVES OF A-30912A NUCLEUS

[75] Inventor: Manuel Debono, Indianapolis, Ind.

[73] Assignee: Eli Lilly and Company, Indianapolis, Ind.

[21] Appl. No.: 181,442

[22] Filed: Aug. 25, 1980

Related U.S. Application Data

[63] Continuation-in-part of Ser. No. 103,012, Dec. 13, 1979, abandoned.

[51] Int. Cl.$^3$ .................................................. C07C 103/52
[52] U.S. Cl. ................................................ 260/112.5 R
[58] Field of Search ................................. 260/112.5 R

[56] References Cited

U.S. PATENT DOCUMENTS

| | | | |
|---|---|---|---|
| 3,150,059 | 9/1964 | Kleinschmidt et al. | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgens et al. | 260/112.5 R |
| 4,050,989 | 9/1977 | Kuwann et al. | 260/112.5 R |
| 4,173,629 | 11/1979 | Dreyfuss et al. | 260/112.5 R |

FOREIGN PATENT DOCUMENTS

| | | | |
|---|---|---|---|
| 568386 | 4/1972 | Belgium | 260/112.5 R |
| 834289 | 10/1974 | Belgium | 260/112.5 R |
| 859067 | 2/1977 | Belgium | 260/112.5 R |
| 866095 | 4/1977 | Belgium | 260/112.5 R |
| 851310 | 8/1977 | Belgium | 260/112.5 R |

OTHER PUBLICATIONS

The Journal of Antibiotics, vol. 29, No. 12, 1339–1340, 1976.
Agr. Biol. Chem., 37(11), 2455–2463, 1973.
Agr. Biol. Chem., 37(12), 2709–2717, 1973.
Agr. Biol. Chem., 38(3), 521–529, 1974.
Agr. Biol. Chem. 38(10), 1767–1777, (1974).
The Journal of Biochemistry, vol. 56, No. 4, 1964, 335–343.
The Journal of Antibiotics, vol. 31, No. 4, 373–374, (1978).
The Journal of Antibiotics, (1975), 764–769, vol. 28, No. 10.
The Journal of Antibiotics, 1976, 380–389, vol. 29, No. 4.
The Journal of Antibiotics, 1976, 1268–1274, vol. 29, No. 12.
The Journal of Antibiotics, vol. 29, No. 12, 1275–1280, 1976.
Helvetica Chimico Acta, vol. 57, fasc. 8, (1974), 2459–2477.
Tetrahedron Letters No. 46, pp. 4147–4150, 1976.
Helvetica Chimico Acta, vol. 62, fasc. 4, (1979), 1252–1266.

*Primary Examiner*—Delbert R. Phillips
*Attorney, Agent, or Firm*—Nancy J. Harrison; Arthur R. Whale

[57] ABSTRACT

Compounds of the formula

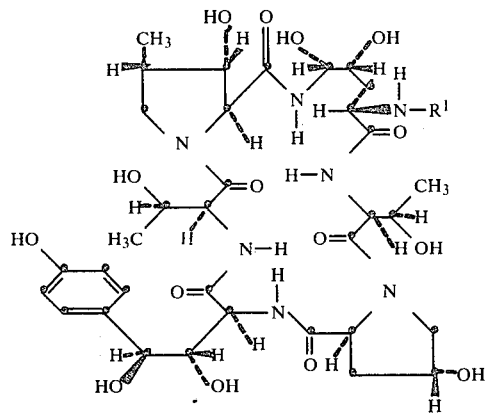

wherein $R^1$ is a group of the formula:

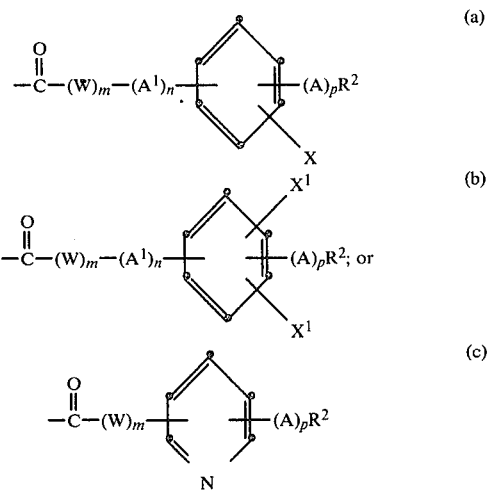

wherein A is divalent oxygen, sulfur, sulfinyl, or sulfonyl; $A^1$ is divalent oxygen, sulfur, sulfinyl, sulfonyl or —NH—; X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl or $C_1$–$C_3$ alkylcarbamyl; $X^1$ is chloro, bromo or iodo; $R^2$ is hydrogen, $C_1$–$C_{18}$ alkyl or $C_2$–$C_{18}$ alkenyl; W is $C_1$–$C_{10}$ alkylene or $C_2$–$C_{10}$ alkenylene; m, n and p are 0 or 1, but if m=0, n must=0; provided: that the sum of the carbon atoms in the $R^2$ and W groups must be greater than 4 but cannot exceed 21; that when X is mercapto. A and $A^1$ cannot be sulfinyl or sulfonyl; and that when A and $A^1$ are sulfinyl or sulfonyl, they must be in equal oxidation states.

40 Claims, No Drawings

DERIVATIVES OF A-30912A NUCLEUS

CROSS-REFERENCE TO RELATED APPLICATION

This application is a continuation-in-part of application Ser. No. 103,012, filed Dec. 13, 1979, now abandoned.

BACKGROUND OF THE INVENTION

This invention relates to novel semi-synthetic antifungal compounds which are prepared by the acylation of the cyclic peptide nucleus produced by the enzymatic deacylation of antibiotic A30912 factor A.

Antibiotic A-30912 factor A is an antifungal cyclic peptide having the formula:

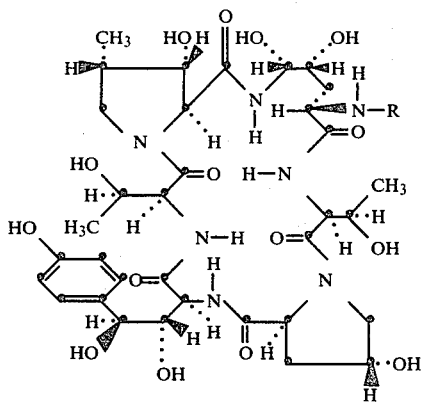

wherein R is the linoleoyl group

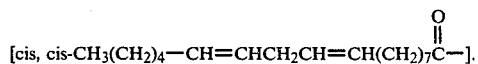

[cis, cis-$CH_3(CH_2)_4$—CH=$CHCH_2CH$=$CH(CH_2)_7\overset{O}{\overset{\|}{C}}$—].

Throughout this application, the cyclic peptide formulas, such as formula I, assume that the amino acids represented are in the L-configuration. The factor is isolated from the A30912 complex which contains other factors arbitrarily designated factors B, C, D, E, F and G. The A-30912 complex and the individual factors A through G are described by M. Hoehn and K. Michel in U.S. Pat. No. 4,024,245. Factor A is identical to antibiotic A-22802 which is described by C. Higgins and K. Michel in U.S. Pat. No. 4,024,246. Factor A has also been found to be identical to antibiotic echinocandin B [see F. Benz et al., *Helv. Chim. Acta,* 57, 2459 (1974) and Swiss Pat. No. 568,386] and to antibiotic SL 7810/F [see C. Keller-Juslen et al. *Tetrahedron Letters,* 4147 (1976) and Belgium Pat. No. 834,289].

Antibiotic A-30912 factor A is prepared by fermentation using one of several different organisms, namely: (a) *Aspergillus rugulosus* NRRL 8113 (see U.S. Pat. No. 4,024,245); (b) *Aspergillus nidulans* NRRL 8112 (see U.S. Pat. No. 4,024,246); (c) *Aspergillus nidulans* var. echinulatus A-32204 as described in Swiss Patent No. 568,386; (d) *Aspergillus rugulosus* NRRL 8039 (see Belgian Pat. No. 834,289); or (e) *Aspergillus nidulans* var. roseus NRRL 11440 [see co-pending application of L. Boeck and R. Kastner, METHOD OF PRODUCING THE A-30912 ANTIBIOTICS, Ser. No. 126,078, filed Mar. 3, 1980, which is a continuation-in-part of application Ser. No. 46,744, filed June 8, 1979 (now abandoned), the entire disclosure of which is incorporated herein by reference].

A subculture of *A. nidulans* var. roseus has been deposited and made a part of the permanent culture collection of the Northern Regional Research Laboratory, U.S. Department of Agriculture, Agricultural Research Service, Peoria, Ill. 61604, from which it is available to the public under the number NRRL 11440.

When a strain of *A. nidulans* var. roseus NRRL 11440 is used to produce A-30912 factor A, a complex of factors is obtained which for convenience is called the A-42355 antibiotic complex. A-30912 factor A is the major factor of the A-42355 antibiotic complex, while factors B, D and H are minor factors. Examples 10, 11, and 12 herein, illustrate the preparation of the A-42355 complex and the isolation and purification of A-30912 factor A therefrom. A-30912 factor H is further described in a co-pending application of Karl H. Michel entitled ANTIBIOTIC A-30912 FACTOR H, Ser. No. 117,739 filed Feb. 1, 1980, which is a continuation-in-part of application Ser. No. 46,875, filed June 8, 1979 (now abandoned).

In the A-30912 factor A molecule (Formula I), the linoleoyl side chain (R) is attached at the cyclic peptide nucleus at the α-amino group of the dihydroxyornithine residue. Surprisingly, it has been found that the linoleoyl side chain can be cleaved from the nucleus by an enzyme without affecting the chemical integrity of the nucleus. The enzyme employed to effect the deacylation reaction is produced by a microorganism of the family Actinoplanaceae, preferably the microorganism *Actinoplanes utahensis* NRRL 12052 or a variant thereof. To accomplish deacylation, antibiotic A30912 factor A is added to a culture of the microorganism, and the culture is allowed to incubate with the substrate until the deacylation is substantially complete. The cyclic nucleus thereby obtained is separated from the fermentation broth by methods known in the art. Unlike antibiotic A-30912 factor A, the cyclic nucleus (lacking the linoleoyl side chain) is substantially devoid of antifungal activity.

The cyclic nucleus afforded by the afore-described enzymatic deacylation of antibiotic A-30912A factor A is depicted in Formula II.

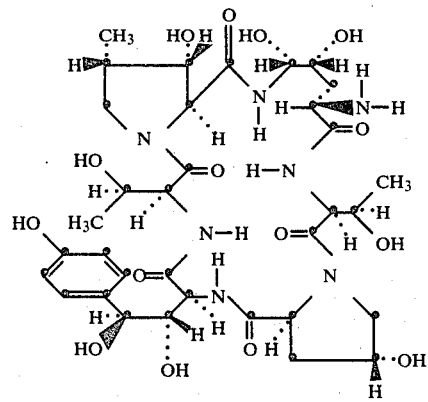

Removal of the side chain group affords a free primary α-amino group in the dihydroxyornithine residue of the cyclic peptide. For convenience, the compound having the structure given in Formula II will be referred to herein as "A-30912A nucleus." As will be apparent to those skilled in the art, A-30912A nucleus can be obtained either in the form of the free amine or of the acid addition salt. Although any suitable acid addition salt may be employed, those which are non-toxic and pharmaceutically acceptable are preferred.

The method of preparing a-30912A nucleus from antibiotic A-30912 factor A by means of fermentation using *Actinoplanes utahensis* NRRL 12052 is described in the co-pending application of Bernard J. Abbott and David S. Fukuda entitled "A-30912A NUCLEUS", Ser. No. 103,017, filed Dec. 13, 1979, continued in an application (Ser. No. 103,012) filed herewith this even date, the full disclosure of which is incorporated herein by reference. Example 7 herein illustrates the preparation of A-30912A nucleus by fermentation using antibiotic A-30912 factor A as the substrate and *Actinoplanes utahensis* NRRL 12052 as the microorganism.

The enzyme produced by *Actinoplanes utahensis* NRRL 12052 may be the same enzyme which has been used to deacylate penicillins (see Walter J. Kleinschmidt, Walter E. Wright, Frederick W. Kavanagh, and William M. Stark, U.S. Pat. No. 3,150,059, issued Sept. 22, 1964).

Cultures of representative species of Actinoplanaceae are available to the public from the Northern Regional Research Laboratory under the following accession numbers:

| | |
|---|---|
| Actinoplanes utahensis | NRRL 12052 |
| Actinoplanes missouriensis | NRRL 12053 |
| Actinoplanes sp. | NRRL 8122 |
| Actinoplanes sp. | NRRL 12065 |
| Streptosporangium roseum var. hollandensis | NRRL 12064 |

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. Loss of antibiotic activity is an indication that the microorganism produces the requisite enzyme for deacylation. This must be verified, however, using one of the following methods: 1) analysis by HPLC for presence of the intact nucleus; or 2) re-acylation with an appropriate side chain (e.g. linoleoyl, stearoyl, or palmitoyl) to restore activity.

It is known that other antibiotic substances possess the same nucleus as that of Antibiotic A-30912 factor A. These antibiotics differ from antibiotic A-30912 factor A in that different acyl groups are present in place of the linoleoyl group (R) in Formula I. Such antibiotics are: (a) tetrahydro-A-30912 factor A (tetrahydro-SL 7810/F; tetrahydro-echinocandin B) described in Belgium Patent 834,289 and by F. Benz et al., *Helv. Chim. Acta*, 57 2459 (1974), which compound is depicted in Formula I when R is stearoyl; and (b) aculeacin A, which is a component of the aculeacin complex (prepared by fermentation using *Aspergillus aculeatus* NRRL 8075) and is described by K. Mizuno et al., in U.S. Pat. No. 3,978,210. As is discussed in Belgium Patent 859,067, in aculeacin A the palmitoyl side chain is present in place of linoleoyl. Tetrahydro-A-30912 factor A can be prepared from antibiotic A-30912 factor A by catalytic hydrogenation using $PtO_2$ in ethanol under positive pressure. Both tetrahydro-A-30912 factor A and aculeacin A can be employed as substrates for the enzymatic deacylation using the procedures herein described.

SUMMARY OF THE INVENTION

The invention sought to be patented comprehends novel compounds derived by acylating the A-30912A nucleus (Formula II). The compounds of the present invention have the chemical structure depicted in Formula III:

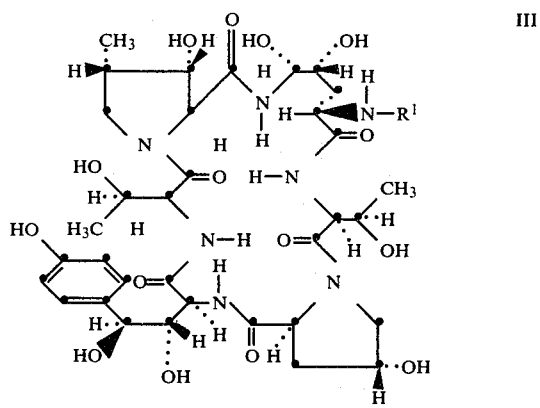

wherein $R^1$ is a group of the formula:

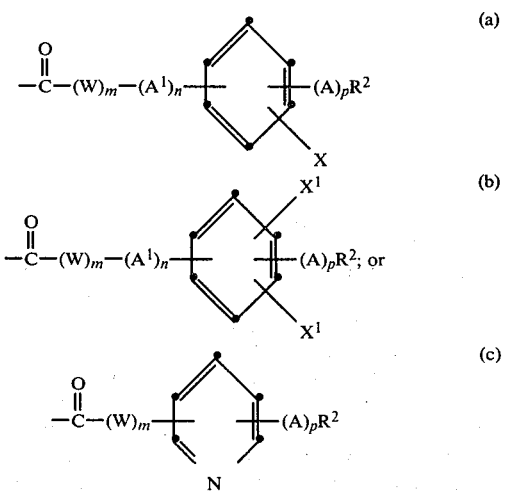

wherein A is divalent oxygen, sulfur, sulfinyl, or sulfonyl; $A^1$ is divalent oxygen, sulfur, sulfinyl, sulfonyl or —NH—; X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl or $C_1$–$C_3$ alkylcarbamyl; $X^1$ is chloro, bromo or iodo; $R^2$ is hydrogen, $C_1$–$C_{18}$ alkyl or $C_2$–$C_{18}$ alkenyl; W is $C_1$–$C_{10}$ alkylene or $C_2$–$C_{10}$ alkenylene; m, n and p are 0 or 1, but if m=0, n must=0; provided: that the sum of the carbon atoms in the $R^2$ and W groups must be greater than 4 but cannot exceed 21; that when X is mercapto, A and $A^1$ cannot be sulfinyl or sulfonyl; and that when A and $A^1$ are sulfinyl or sulfonyl, they must be in equal oxidation states.

A preferred subgroup of formula III compounds are those of group (a) wherein m and n=0, p=1, and $R^2$ is $C_5$–$C_{18}$ alkyl or $C_5$–$C_{18}$ alkenyl.

It will be recognized by those skilled in the art that in the substituted ring of the $R^1$ group, the

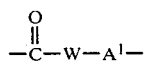

function and the —$AR^2$ function may be oriented on the benzene ring in the ortho, meta, or para position relative to each other. The para orientation for these groups is preferred. The substituent represented by X may be substituted at any available position of the benzene ring not occupied by these two groups.

As employed herein, the term "alkyl" or "alkenyl" comprehend both straight and branched hydrocarbon chains. By "alkenyl" is meant an unsaturated hydrocarbon group containing one, two, or three double bonds which may be either in the cis or trans configuration.

Illustrative $C_5$–$C_{18}$ alkyl radicals which are preferred for $R^2$ for the purposes of this invention are:

(a) —$(CH_2)_{n'}CH_3$ wherein n' is in integer from 4 to 17; and (b)

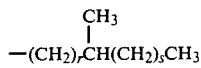

wherein r and s are, independently, an integer from 0 to 15, provided that r+s can be no greater than 15 or no less than 2.

Illustrative $C_5$–$C_{18}$ alkenyl radicals, which are preferred for $R^2$ for the purposes of this invention, are:

(a) —$(CH_2)_t$—CH=CH—$(CH_2)_{n'''}$—$CH_3$ wherein t is an integer from 1 to 15, and n" is an integer from 0 to 15 provided that t+n" can be no greater than 15 or no less than 2; and (b) —$(CH_2)_v$—CH=CH—$(CH_2)_y$—CH=CH—$(CH_2)_z$—$CH_3$ wherein v and z are, independently, an integer from 0 to 12 and y is an integer from 0 to 13 provided that v+y+z must be no greater than 13.

Illustrative $C_1$–$C_{10}$-alkylene radicals, which are preferred W groups for the purposes of this invention, are:

(a) —$(CH_2)_{n''''}$— wherein n''' is an integer from 1 to 10;

(b) methylene and ethylene; and (c)

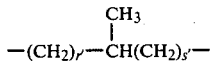

wherein r' and s' are, independently, integers from 0 to 8, provided that r'+s' can be no greater than 8 or no less than 1.

Illustrative $C_2$–$C_{10}$-alkenylene radicals, which are preferred W groups for the purposes of this invention, are:

(a) —$(CH_2)_{t'}$—CH=CH—$(CH_2)_{v'}$- wherein t' and v' are, independently, integers from 0 to 8, provided that t'+v' must be no greater than 8;

(b) —$(CH_2)_{x'}$—CH=CH—$(CH_2)_{y'}$—CH=CH—$(CH_2)_{z'}$— wherein x' and z' are, independently, integers from 0 to 5, and y' is an integer from 1 to 5, provided that x'+y'+z' must be no greater than 10.

DETAILED DESCRIPTION OF THE INVENTION

The compounds of Formula III inhibit the growth of pathogenic fungi as evidenced by standard biological test procedures. The compounds are useful, therefore, for controlling the growth of fungi on environmental surfaces (as an antiseptic) or in treating infections caused by fungi. The antifungal activity of the compounds has been demonstrated against *Candida albicans* in vitro in agar plate disc diffusion tests or agar tube dilution tests, or in vivo in tests in mice infected with *C. albicans*. Thus, the compounds are particularly useful in treating infections caused by strains of *C. albicans* (candidosis). The compounds of Formula III have also shown activity in vitro in agar-plate disc diffusion tests against *Trichophyton mentagrophytes*, a dermatophytic organism. Activity has also been found in in vitro agar-plate disc-diffusion tests against *Saccharomyces pastorianus*, and *Neurospora crassa*. Certain compounds (as shown in Example 6, Table 9) give significant blood levels upon oral administration in mice.

When given to a dog by intravenous administration, 100 mg/kg per day for five days, the compound of Formula III wherein $R^1$ is p-(n-octyloxy)benzoyl showed no outward signs of toxicity, although increased SGPT levels were observed.

The compounds of Formula III are prepared by acylating A-30912A nucleus at the α-amino group of dihydroxynithine with the appropriate side chain using methods conventional in the art for forming an amide bond. The acylation is accomplished, in general, by reacting the nucleus with an activated derivative of the substituted compound of Formula IV (a), (b) or (c) corresponding to the desired acyl side chain group ($R^1$).

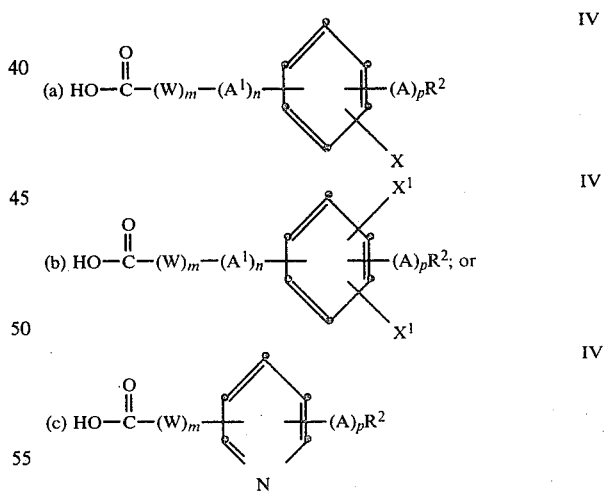

(A, $A^1$, W, m, n, p and $R^2$ have the meanings herein described supra.)

By the term "activated derivative" is meant a derivative which renders the carboxyl function of the acylating agent reactive to coupling with the primary amino group to form the amide bond which links the side chain to the nucleus. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. an alkoxyformic acid anhydride or aryloxyformic acid anhydride) or (c) an activated ester (e.g. a 2,4,5-trichlorophenyl ester, an N-hydroxybenztriazole ester, or an N-hydroxysuccinimide ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of Formula III is by the active ester method. The use of the 2,4,5-trichlorophenyl ester of the desired side chain acid (Formula IV) as the acylating agent is most preferred. In this method, an excess amount of the active ester is reacted with the nucleus at room temperature in a non-reactive organic solvent such as dimethylformamide (DMF). The reaction time is not critical, although a time of about 24 to about 120 hours is preferred. At the conclusion of the reaction, the solvent is removed, and the residue is purified by chromatography, such as over silica gel using ethyl acetate-methanol (3:2, v/v) as the eluent, or by reversed phase HPLC using silica gel $C_{18}$ reversed phase resin as the stationary phase and a mixture of $H_2O/CH_3OH/CH_3CN$ as the solvent system.

The 2,4,5-trichlorophenyl esters are conveniently made by treating the side chain acid (Formula IV) with 2,4,5-trichlorophenol in the presence of a coupling agent, such as N,N'-dicyclohexylcarbodiimide. Other methods of preparation of the active esters will be apparent to those skilled in the art.

The substituted acids of Formula IV, and the activated derivatives thereof, are either known compounds or they can be made from known compounds by methods known in the art. The benzoic, phenylalkylcarboxylic, phenylalkenylcarboxylic, phenoxyalkylcarboxylic, phenoxyalkenylcarboxylic, phenylthioalkylcarboxylic, phenylthioalkenylcarboxylic, phenylsulfinylalkylcarboxylic, phenylsulfinylalkenylcarboxylic, phenylsulfonylalkylcarboxylic, phenylsulfonylalkenylcarboxylic, pyridinylcarboxylic, pyridinylalkylcarboxylic, and pyridinylalkenylcarboxylic acids of Formula IV are prepared by similar procedures. To illustrate these procedures, a discussion of the preparation of the benzoic acid subgroup is provided.

The alkoxybenzoic acids or alkenyloxybenzoic acids can be prepared conveniently from an appropriate hydroxybenzoic acid by reacting an appropriate alkyl or alkenyl halide with the disodium salt of the appropriate hydroxybenzoic acid. The (alkylthio)benzoic acids or the (alkenylthio)benzoic acids can be prepared conveniently by treating the appropriate substituted S-(4-carbomethoxyphenyl)dimethylthiocarbamate of the general formula $CH_3CO_2C_6H_3XS(CO)N(CH_3)_2$ with aqueous sodium hydroxide at 65°–85° C., then adding the appropriate alkyl or alkenyl bromide, and continuing heating for 2–4 hours. The substituted S-(4-carbomethoxyphenyl)dimethylthiocarbamates can be made from the appropriate hydroxybenzoic acids by the method of M. Newman and H. Kanes, *J. Org. Chem.*, 31, 3980 (1966).

When it is desired to prepare a compound of Formula III wherein A is sulfinyl or sulfonyl, the appropriate sulfoxide or sulfone derivative of the (alkenylthio)- or (alkylthio)benzoic acid (Formula IV) can be employed for acylation of the nucleus. The appropriate sulfoxides or sulfones can be made by oxidation of the corresponding thioether compound using conventional agents, such as m-chloroperbenzoic acid, t-butylhypochlorite, sodium metaperiodate, or hydrogen peroxide. If a double bond is present in the thioether, very mild conditions should be employed to avoid epoxidation. If equimolar amounts of reactants are taken, the product is a sulfoxide (A is sulfinyl), which is readily oxidized to the sulfone (A is sulfonyl) by an additional mole of the oxidizing agent. The hydroxybenzoic acids and substituted derivatives thereof used as starting material in the processes described herein are either known compounds or can be prepared by conventional methods which are known in the art.

When employed systemically, the dosage of the compounds of Formula III will vary according to the particular compound being employed, the severity and nature of the infection, and the physical condition of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose may be added to make the solutions isotonic. The proportions and nature of such additives will be apparent to those skilled in the art.

Certain compounds of Formula III give significant blood levels after oral administration (see Example 6, Table 9) and can be administered systemically by the oral route. For oral use, such compounds can be administered in combination with pharmaceutically acceptable carriers or excipients in the form of capsules, tablets or powders. The nature and proportion of such carriers or excipients will be recognized by those skilled in the art.

When employed to treat vaginal candida infections, the compounds of Formula III can be administered in combination with pharmaceutically acceptable conventional excipients suitable for intravaginal use. Formulations adapted for intravaginal administration will be known to those skilled in the art.

The methods of making and using the compounds of the present invention are illustrated in the following examples:

EXAMPLE 1

Tables 1 through 7 below, give the preparation, respectively, of various alkoxybenzoic acids, (alkylthio)benzoic acids, alkoxyphenylacetic acids, alkoxyphenylpropanoic acids, alkoxycinnamic acids, alkoxyphenoxyacetic acids, and alkoxynicotinic acids.

The preparation of these formula IV acids is typified by the preparation of the alkoxybenzoic acids of Table 1 and the (alkylthio)benzoic acids of Table 2. The general procedure for the preparation of these acids is described in the following paragraphs.

The alkoxybenzoic acids set forth in Table 1 are prepared according to the following general procedure:

p-Hydroxybenzoic acid is dissolved in 10% aqueous sodium hydroxide (two equivalents), and the resulting solution is added to dimethyl sulfoxide (DMSO) (200 ml). The alkyl bromide (one equivalent) is added to the solution at 65°–80° C. The solution is then stirred for two hours after which it is poured into a large volume (600 ml.) of water and acidified with hydrochloric acid.

The alkoxybenzoic acid, which precipitates from the solution, is collected by filtration and crystallized from methanol.

The (alkylthio)benzoic acids set forth in Table 2 are prepared according to the following general procedure: To a suspension of sodium hydride (one equivalent, 50% dispersion in mineral oil) in DMF (100 ml per 50 mmole), cooled to 0° C., is added slowly methyl p-hydroxybenzoate (one equivalent). The reaction mixture is stirred under a nitrogen atmosphere until the evolution of hydrogen ceases. To the solution of sodium 4-carbomethoxyphenolate so produced, is added N,N-dimethylthiocarbamoyl chloride [$(CH_3)_2N(CS)Cl$] (one equivalent) in one portion. The resulting suspension is heated to 70° C. for 1-3 hours and then is poured into an aqueous solution (1%) of potassium hydroxide (large excess). The suspension is extracted twice with toluene-hexane (4:1 v/v). After drying over $MgSO_4$, the organic extracts are filtered and evaporated to an oil. The oil is purified by chromatography over silica gel using 2% methanol in methylene chloride to give O-(4-carbomethoxyphenyl)dimethylthiocarbamate [p-$CH_3CO_2C_6H_4O$ $(CS)N(CH_3)_2$]. (mp 97°-102° C.). This product is heated under a nitrogen atmosphere at 220° C. for 30-60 min. to give S-(4-carbomethoxyphenyl)-dimethylthiocarbamate [p-$CH_3CO_2C_6H_4S(-CO)N(CH_3)_2$] which is crystallized from methanol. To S-(4-carbomethoxyphenyl)dimethylthiocarbamate, dissolved in DMSO, is added 2 equiv. of sodium hydroxide (10% aqueous). The mixture is heated at 65°-85° C., and the alkyl bromide (1 equiv.) is added. Heating is continued for 2-4 hours after which the mixture is poured into a large volume of water. Upon acidification, a precipitate forms, which is collected by filtration. The (alkylthio)benzoic acid is crystallized from methanol.

TABLE 1

Preparation of Alkoxybenzoic Acids

| Alkyl Bromide | | Weight of | Alkoxybenzoic Acid | |
|---|---|---|---|---|
| Formula | Weight | p-Hydroxybenzoic Acid | Formula | Weight |
| $CH_3(CH_2)_7Br$ | 9.65 g. | 6.9 g. | $CH_3(CH_2)_7O$—C$_6$H$_4$—$CO_2H$ | 6.18 g. |
| $CH_3(CH_2)_9Br$ | 11.05 g. | 6.9 g. | $CH_3(CH_2)_9O$—C$_6$H$_4$—$CO_2H$ | 6.79 g. |
| $CH_3(CH_2)_{13}Br$ | 13.85 g. | 6.9 g. | $CH_3(CH_2)_{13}O$—C$_6$H$_4$—$CO_2H$ | 6.18 g. |
| $CH_3(CH_2)_7Br$ | 9.1 g. | 6.4 g. | $CH_3(CH_2)_7O$—C$_6$H$_4$—$CO_2H$ | 6.69 g. |
| $CH_3(CH_2)_9Br$ | 10.8 g. | 6.4 g. | $CH_3(CH_2)_9O$—C$_6$H$_4$—$CO_2H$ | 10.2 g. |
| $CH_3(CH_2)_{11}Br$ | 11.7 g. | 6.4 g. | $CH_3(CH_2)_{11}O$—C$_6$H$_4$—$CO_2H$ | 10.9 g. |
| $CH_3(CH_2)_{13}Br$ | 13.0 g. | 6.4 g. | $CH_3(CH_2)_{13}O$—C$_6$H$_4$—$CO_2H$ | 7.3 g. |

TABLE 2

Preparation of Alkylthiobenzoic Acids

| Alkyl Bromide | | Weight of S-(4-carbomethoxyphenyl)- | Alkylthiobenzoic Acid | |
|---|---|---|---|---|
| Formula | Weight | dimethylthiocarbamate | Formula | Weight |
| $CH_3(CH_2)_7Br$ | 386 mg. | 478 mg. | $CH_3(CH_2)_7S$—C$_6$H$_4$—$CO_2H$ | 405 mg. |
| $CH_3(CH_2)_9Br$ | 1.77 g. | 1.91 g. | $CH_3(CH_2)_9S$—C$_6$H$_4$—$CO_2H$ | 1.34 g. |
| $CH_3(CH_2)_{11}Br$ | 1.99 g. | 1.99 g. | $CH_3(CH_2)_{11}S$—C$_6$H$_4$—$CO_2H$ | 1.8 g. |
| $CH_3(CH_2)_{13}Br$ | 2.22 g. | 1.91 g. | $CH_3(CH_2)_{13}S$—C$_6$H$_4$—$CO_2H$ | 2.3 g. |

TABLE 3

Preparation of Alkoxyphenylacetic Acids

| Alkyl Bromide | | Weight of | Alkoxyphenylacetic Acid | |
|---|---|---|---|---|
| Formula | Weight | Hydroxyphenylacetic Acid | Formula | Weight |
| $CH_3(CH_2)_7Br$ | 3.86 g. | 3.04 g. | $CH_3(CH_2)_7O$—C$_6$H$_4$—$CH_2CO_2H$ | 2.56 g. |

TABLE 3-continued

Preparation of Alkoxyphenylacetic Acids

| Alkyl Bromide | | Weight of | Alkoxyphenylacetic Acid | |
|---|---|---|---|---|
| Formula | Weight | Hydroxyphenylacetic Acid | Formula | Weight |
| $CH_3(CH_2)_{11}Br$ | 4.98 g. | 3.04 g. | $CH_3(CH_2)_{11}O$—⟨benzene⟩—$CH_2CO_2H$ | 3.70 g. |
| $CH_3(CH_2)_7Br$ | 3.86 g. | 3.04 g. | $CH_3(CH_2)_7O$—⟨benzene⟩—$CH_2CO_2H$ | 3.72 g. |
| $CH_3(CH_2)_{11}Br$ | 4.98 g. | 3.04 g. | $CH_3(CH_2)_{11}O$—⟨benzene⟩—$CH_2CO_2H$ | 2.72 g. |
| $CH_3(CH_2)_7Br$ | 3.56 g. | 3.04 g. | $CH_3(CH_2)_7O$—⟨benzene⟩ with $HO_2C$—$CH_2$ | 1.87 g. |

TABLE 4

Preparation of Alkoxyphenylpropanoic Acids

| Alkyl Bromide | | Weight of p-Hydroxyphenylpropanoic Acid | Alkoxyphenylpropanoic Acid | |
|---|---|---|---|---|
| Formula | Weight | | Formula | Weight |
| $CH_3(CH_2)_3Br$ | 2.74 g. | 3.32 g. | $CH_3(CH_2)_3O$—⟨benzene⟩—$(CH_2)_2$—$CO_2H$ | 2.97 g. |
| $CH_3(CH_2)_4Br$ | 3.02 g. | 3.32 g. | $CH_3(CH_2)_4O$—⟨benzene⟩—$(CH_2)_2$—$CO_2H$ | 2.80 g. |
| $CH_3(CH_2)_5Br$ | 3.30 g. | 3.32 g. | $CH_3(CH_2)_5O$—⟨benzene⟩—$(CH_2)_2$—$CO_2H$ | 3.53 g. |
| $CH_3(CH_2)_6Br$ | 3.58 g. | 3.32 g. | $CH_3(CH_2)_6O$—⟨benzene⟩—$(CH_2)_2$—$CO_2H$ | 2.90 g. |
| $CH_3(CH_2)_7Br$ | 5.79 g. | 4.98 g. | $CH_3(CH_2)_7O$—⟨benzene⟩—$(CH_2)_2$—$CO_2H$ | 4.65 g. |
| $CH_3(CH_2)_{11}Br$ | 7.47 g. | 4.98 g. | $CH_3(CH_2)_{11}O$—⟨benzene⟩—$(CH_2)_2$—$CO_2H$ | 4.01 g. |

TABLE 5

Preparation of Alkoxycinnamic Acids

| Alkyl Bromide | | Weight of | Alkoxycinnamic Acid | |
|---|---|---|---|---|
| Formula | Weight | p-Hydroxycinnamic Acid | Formula | Weight |
| $CH_3(CH_2)_5Br$ | 3.30 g. | 3.28 g. | $CH_3(CH_2)_5O$—⟨benzene⟩—$CH=CH$—$CO_2H$ | 2.04 g. |
| $CH_3(CH_2)_7Br$ | 3.86 g. | 3.28 g. | $CH_3(CH_2)_7O$—⟨benzene⟩—$CH=CH$—$CO_2H$ | 2.75 g. |
| $CH_3(CH_2)_9Br$ | 4.42 g. | 3.28 g. | $CH_3(CH_2)_9O$—⟨benzene⟩—$CH=CH$—$CO_2H$ | 1.48 g. |

TABLE 6

Preparation of Alkoxyphenoxyacetic Acids

| Alkyl Bromide | | Weight of p-Hydroxyphenoxyacetic Acid | Alkoxyphenoxyacetic Acid | |
|---|---|---|---|---|
| Formula | Weight | | Formula | Weight (g) |
| $CH_3(CH_2)_7Br$ | 3.86 g. | 2.36 g. | $CH_3(CH_2)_7$—$O$—⟨benzene⟩—$OCH_2CO_2H$ | 3.4 |
| $CH_3(CH_2)_9Br$ | 4.42 g. | 2.36 g. | $CH_3(CH_2)_9$—$O$—⟨benzene⟩—$OCH_2CO_2H$ | 3.8 |

TABLE 7

Preparation of Alkoxynicotinic Acids

| Alkyl Bromide | | Weight of | Alkoxynicotinic Acid | |
|---|---|---|---|---|
| Formula | Weight | 6-Hydroxynicotinic Acid | Formula | Weight |
| $CH_3(CH_2)_7Br$ | 3.86 g. | 2.78 g. | $CH_3(CH_2)_7-O-\text{[pyridine]}-CO_2H$ | 3.6 g. |
| $CH_3(CH_2)_{11}Br$ | 4.98 g | 2.78 g. | $CH_3(CH_2)_{11}-O-\text{[pyridine]}-CO_2H$ | 2.4 g. |

EXAMPLE 2

Table 8, below, gives the preparation of the 2,4,5-trichlorophenyl esters of a number of Formula IV acids, including the alkoxybenzoic acids shown in Table 1 and the (alkylthio)benzoic acids shown in Table 2. The compounds set forth in Table 8 are prepared according to the same general procedure. The following procedure is illustrative:

The alkoxybenzoic acid or (alkylthio)benzoic acid (1 mole), 2,4,5-trichlorophenol (1.1 mole), and N,N'-dicyclohexylcarbodiimide (1 mole) are dissolved in methylene chloride. The mixture is stirred at room temperature for 15–18 hours after which it is filtered. The filtrate is evaporated to dryness under reduced pressure, and the residue is crystallized from acetonitrile-water. The product is dried under vacuum.

TABLE 8

Preparation of 2,4,5-Trichlorophenyl Esters

| Formula IV Acid Formula | Weight (g) | Weight of 2,4,5-Trichlorophenyl Ester (g) |
|---|---|---|
| $CH_3(CH_2)_7O-\text{[phenyl]}-CO_2H$ | 6.18 | 5.32 |
| $CH_3(CH_2)_9O-\text{[phenyl]}-CO_2H$ | 6.79 | 1.93 |
| $CH_3(CH_2)_{11}O-\text{[phenyl]}-CO_2H$* | 3.06 | 2.20 |
| $CH_3(CH_2)_{13}O-\text{[phenyl]}-CO_2H$ | 6.90 | 5.91 |
| $CH_3(CH_2)_7S-\text{[phenyl]}-CO_2H$ | 6.43 | 7.98 |
| $CH_3(CH_2)_9S-\text{[phenyl]}-CO_2H$ | 1.34 | 1.42 |
| $CH_3(CH_2)_{11}S-\text{[phenyl]}-CO_2H$ | 1.8 | 2.5 |
| $CH_3(CH_2)_{13}S-\text{[phenyl]}-CO_2H$ | 2.3 | 2.8 |
| $CH_3(CH_2)_7-O-\text{[furan]}-CO_2H$ | 3.75 | 4.72 |
| $CH_3(CH_2)_9-O-\text{[furan]}-CO_2H$ | 4.17 | 5.7 |
| $CH_3(CH_2)_{11}-O-\text{[furan]}-CO_2H$ | 4.59 | 5.0 |
| $CH_3(CH_2)_{13}-O-\text{[furan]}-CO_2H$ | 5.01 | 8.6 |
| $CH_3(CH_2)_7-O-\text{[furan]}-CH_2CO_2H$ | 2.12 | 1.91 |
| $CH_3(CH_2)_{11}-O-\text{[furan]}-CH_2CO_2H$ | 3.2 | 2.36 |
| $CH_3(CH_2)_7-O-\text{[furan]}-CH_2CO_2H$ (isomer) | 2.64 | 2.86 |
| $CH_3(CH_2)_{11}-O-\text{[furan]}-CH_2CO_2H$ (isomer) | 2.0 | 1.65 |
| $CH_3(CH_2)_7-O-\text{[furan(HO_2CCH_2)]}$ | 1.8 | 1.73 |
| $CH_3(CH_2)_3-O-\text{[phenyl]}-(CH_2)_2-CO_2H$ | 2.8 | 3.98 |
| $CH_3(CH_2)_4-O-\text{[phenyl]}-(CH_2)_2-CO_2H$ | 2.36 | 2.82 |
| $CH_3(CH_2)_5-O-\text{[phenyl]}-(CH_2)_2-CO_2H$ | 3.4 | 4.11 |
| $CH_3(CH_2)_6-O-\text{[phenyl]}-(CH_2)_2-CO_2H$ | 2.73 | 2.01 |
| $CH_3(CH_2)_7-O-\text{[phenyl]}-(CH_2)_2-CO_2H$ | 2.78 | 4.3 |
| $CH_3(CH_2)_9-O-\text{[phenyl]}-CH=CH-CO_2H$ | 1.45 | 0.826 |
| $CH_3(CH_2)_{11}-O-\text{[phenyl]}-(CH_2)_2-CO_2H$ | 3.34 | 4.86 |
| $CH_3(CH_2)_5-O-\text{[pyridine]}-CO_2H$* | 2.22 | 2.6 |
| $\text{[pyridine]}-(CH_2)_{10}-CO_2H$* | 2.65 | 3.06 |
| $CH_3(CH_2)_5-O-\text{[furan]}-CH=CHCO_2H$ | 2.0 | 2.84 |
| $CH_3(CH_2)_7-O-\text{[furan]}-CH=CHCO_2H$ | 2.75 | 3.7 |

TABLE 8-continued
Preparation of 2,4,5-Trichlorophenyl Esters

| Formula IV Acid Formula | Weight (g) | Weight of 2,4,5-Trichlorophenyl Ester (g) |
|---|---|---|
| $CH_3(CH_2)_7$—O—⟨benzene⟩—O—$CH_2CO_2H$ | 2.8 | 2.7 |
| $CH_3(CH_2)_9$—O—⟨benzene⟩—$OCH_2CO_2H$ | 3.08 | 2.4 |
| $CH_3(CH_2)_7$—O—⟨pyridine⟩—$CO_2H$ | 2.5 | 2.6 |
| $CH_3(CH_2)_{11}$—O—⟨pyridine⟩—$CO_2H$ | 2.0 | 2.6 |

*Commercially available

EXAMPLE 3

Table 9, below, gives the preparation of the derivatives of A30912A nucleus prepared from the 2,4,5-trichlorophenyl esters set forth in Table 8. The derivatives of A30912A nucleus set forth in Table 9 are prepared in general according to the following procedure:

To A30912A nucleus, dissolved in DMF (10–50 ml.), is added the 2,4,5-trichlorophenyl ester of the alkoxybenzoic acid or the (alkylthio)benzoic acid (1:2 molar ratio). The reaction mixture is stirred for 15–18 hours after which it is taken to dryness to give a residue. The residue is washed (two times each) with a mixture of diethyl ether (50 ml) and methylene chloride (50 ml). The washings are discarded. The remaining residue is dissolved in ethyl acetate-methanol (3:2, v/v) and is chromatographed on a 100 ml. silica gel (Woelm, 70–150 ml.) column using the aforesaid solvent system as the eluent. The fractions from the chromatography are monitored by TLC on silica gel (Merck) using ethyl acetate-methanol (3:2, v/v) as the solvent system. Fractions containing the desired product are combined, and solvent is removed to give the product as a residue. The product may be analyzed by reverse phase HPLC as follows: In the alkoxy examples and the $C_{12}$ and $C_{14}$ alkylthio examples, the sample is dissolved in $H_2O$/$CH_3OH$/$CH_3CN$ (1:2:2 v/v). The sample solution (1 mg/ml) is injected into a ¼ in. by 12 in. stainless steel column packed with $C_{18}$ Micro Bondapak resin (Waters Associates, Milford, Mass.), and the column is eluted with a solvent system comprising $H_2O$/$CH_3OH$/$CH_3CN$ (1:2:2 v/v). In the $C_8$ and $C_{10}$ alkylthio examples, the solvent system is $H_2O$/$CH_3OH$/$CH_3CN$ (2:1:2 v/v). The elution is performed at a pressure of 1500 psi with a flow rate of 3 ml./minute using a Waters 600A pump (Waters Associates, Inc.) and chart speed of 0.2 in./minute. Eluent is monitored with a Varian Vari-Chrom UV detector at 230 nm. The products may also be analyzed by field desorption mass spectrometry (FDMS).

TABLE 9
Preparation of Formula III Derivatives of A-30912A Nucleus

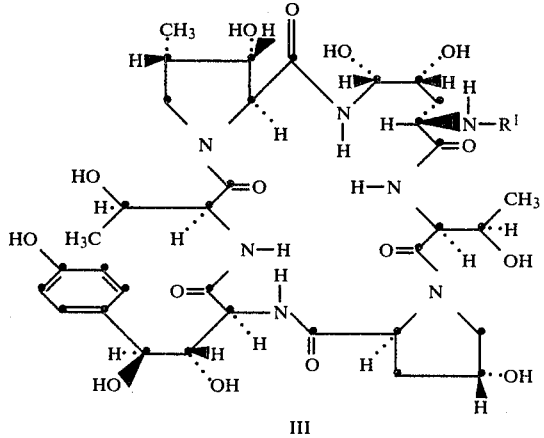

III

| $R^1$ of Formula III | Ester Reactant (mg) | A30912A Nucleus (mg) | Product (mg) | $M^+[Na]^+$ | HPLC Retention (cm) |
|---|---|---|---|---|---|
| $CH_3(CH_2)_7O$—⟨benzene⟩—CO— | 430 | 400 | 103 | 1052 | 0.95 |
| $CH_3(CH_2)_9O$—⟨benzene⟩—CO— | 460 | 400 | 82 | 1080 | 1.55 |
| $CH_3(CH_2)_{11}O$—⟨benzene⟩—CO— | 490 | 400 | 162 | 1107 | 3.50 |
| $CH_3(CH_2)_{13}O$—⟨benzene⟩—CO— | 514 | 400 | 159 | 1135 | 6.6 |
| $CH_3(CH_2)_7S$—⟨benzene⟩—CO— | 446 | 400 | 266 | 1068 | 2.45 |

TABLE 9-continued

Preparation of Formula III
Derivatives of A-30912A Nucleus

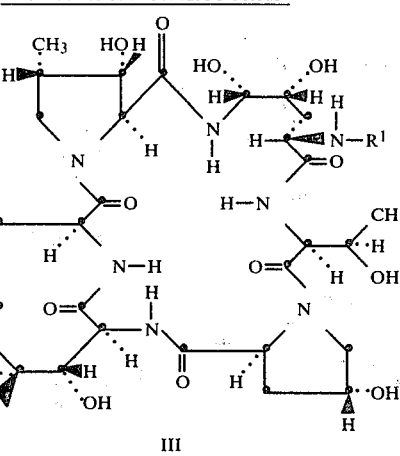

III

| $R^1$ of Formula III | Ester Reactant (mg) | A30912A Nucleus (mg) | Product (mg) | $M^+[Na]^+$ | HPLC Retention (cm) |
|---|---|---|---|---|---|
| $CH_3(CH_2)_9S-\langle\rangle-CO-$ | 474 | 400 | 228 | 1096 | 5.15 |
| $CH_3(CH_2)_{11}S-\langle\rangle-CO-$ | 500 | 400 | 293 | 1124 | 2.5 |
| $CH_3(CH_2)_{13}S-\langle\rangle-CO-$ | 530 | 400 | 266 | 1152 | 4.1 |
| $CH_3(CH_2)_9O-\langle\rangle-CH=CH-CO-$ | 483 | 400 | 190 | 1083 | 11.2 |
| $CH_3(CH_2)_7O-\langle\rangle-CO-$ | 800 | 800 | 920 | 1052 | 1.6 |
| $CH_3(CH_2)_9O-\langle\rangle-CO-$ | 800 | 800 | 740 | 1080 | 3.4 |
| $CH_3(CH_2)_{11}O-\langle\rangle-CO-$ | 800 | 800 | 780 | 1108 | 8.8 |
| $CH_3(CH_2)_{13}O-\langle\rangle-CO-$ | 800 | 800 | 650 | 1136 | 23.7 |
| $CH_3(CH_2)_7O-\langle\rangle-CH_2CO-$ | 444 | 400 | 284 | 1066 | 2.2 |
| $CH_3(CH_2)_{11}O-\langle\rangle-CH_2CO-$ | 1000 | 400 | 178 | 1123 | 8.5 |
| $CH_3(CH_2)_7O-\langle\rangle-CH_2CO-$ | 886 | 400 | 282 | 1066 | 1.5 |
| $CH_3(CH_2)_{11}O-\langle\rangle-CH_2CO-$ | 500 | 400 | 262 | 1123 | 5.2 |
| $CH_3(CH_2)_7O-\langle\rangle\,CH_2CO-$ | 888 | 400 | 230 | 1066 | 4.4 |
| $CH_3(CH_2)_5O-\langle\rangle-CO-$ | 600 | 400 | 245 | 1024 | 1.2 |
| $\langle\rangle-(CH_2)_{10}-CO-$ | 662 | 400 | 230 | 1064 | 2.4 |
| $CH_3(CH_2)_5O-\langle\rangle-CH=CH-CO-$ | 854 | 400 | 301 | 1050 | 3.2 |

TABLE 9-continued
Preparation of Formula III Derivatives of A-30912A Nucleus

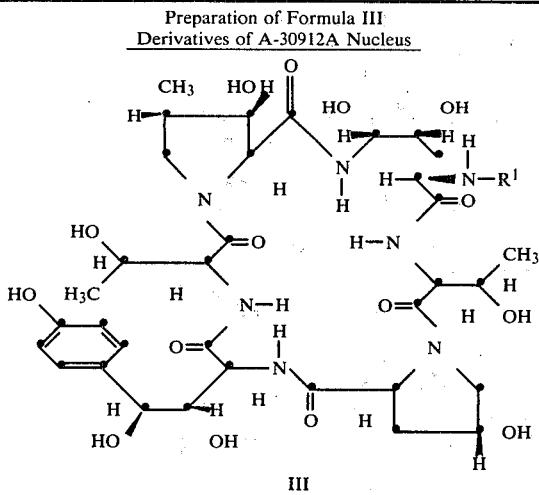

III

| R[1] of Formula III | Ester Reactant (mg) | A30912A Nucleus (mg) | Product (mg) | M+[Na]+ | HPLC Retention (cm) |
|---|---|---|---|---|---|
| CH₃(CH₂)₇O—⟨ ⟩—CH=CH—CO— | 910 | 400 | 98 | 1078 | 9.5 |
| CH₃(CH₂)₇O—⟨ ⟩—O—CH₂—CO— | 918 | 400 | 260 | 1082 | 1.8 |
| CH₃(CH₂)₉O—⟨ ⟩—O—CH₂—CO— | 488 | 400 | 280 | 1110 | 2.7 |
| CH₃(CH₂)₇O—⟨N⟩—CO— | 430 | 400 | 352 | 1053 | 1.0 |
| CH₃(CH₂)₁₁O—⟨N⟩—CO— | 487 | 400 | 270 | 1109 | 2.1 |
| CH₃(CH₂)₇—⟨ ⟩—CO— | 800* | 800 | 460 | 1036 | 3.6 |
| CH₃(CH₂)₇—S(O)—⟨ ⟩—CO— | 922 | 800 | 145 | 1083 | 1.0 |
| CH₃(CH₂)₃O—⟨ ⟩—(CH₂)₂—CO— | 802 | 400 | 320 | 1024 | 1.0 |
| CH₃(CH₂)₄O—⟨ ⟩—(CH₂)₂—CO— | 831 | 400 | 245 | 1038 | 1.2 |
| CH₃(CH₂)₅O—⟨ ⟩—(CH₂)₂—CO— | 858 | 400 | 303 | 1052 | 2.6 |
| CH₃(CH₂)₆O—⟨ ⟩—(CH₂)₂—CO— | 888 | 400 | 191 | 1066 | 2.1 |
| CH₃(CH₂)₇O—⟨ ⟩—(CH₂)₂—CO— | 914 | 400 | 335 | 1081 | 1.2 |
| CH₃(CH₂)₁₁O—⟨ ⟩—(CH₂)₂—CO— | 1030 | 400 | 360 | 1136 | 3.0 |

*p-(n-Octyl)benzoyl chloride (commercially available) was used in this case, reacting the acid chloride with the nucleus in pyridine at room temperature under nitrogen for 24 hours.

EXAMPLE 4

The following procedure illustrates the preparation of the compounds of Formula III wherein A is sulfonyl or sulfinyl.

A. Preparation of p-(Alkylsulfonyl)benzoic Acid 2,4,5-Trichlorophenyl Ester

To a solution of 2,4,5-trichlorophenyl p-(n-decylthio)benzoate (970 mg., 2 mmole) in methylene chloride (20 ml) cooled in an ice bath is added m-chloroperbenzoic acid (442 mg, 2.0 mmole). After allowing the reaction mixture to warm to room temperature (15 minutes), it is washed twice with 0.1 N sodium hydroxide (25 ml). The organic phase, after drying over anhyd. $Na_2SO_4$, is crystallized from acetonitrile. Weight of product: 470 mg. The product is reoxidized as described above using m-chloroperbenzoic acid (108 mg) in methylene chloride (20 ml) and a reaction time of 50 minutes. The product is purified as described above to give 260 mg. of product.

Analysis for $C_{23}H_{27}O_4Cl_3S$: Calculated: C, 54.61%; H, 5.38%. Found: C, 54.90%; H, 5.45%.

Other p-(alkylsulfonyl)benzoic acid 2,4,5-trichlorophenyl esters can be prepared by the above-described methods as shown below:

| p-Alkylsulfonyl benzoic acid 2,4,5-trichlorophenyl ester | Wt. of ester (mg) reactant | Wt. of oxidizing agent (mg) | Wt. of product (mg) |
|---|---|---|---|
| n-octyl | 850 | 451 | 68.8 |
| n-dodecyl | 1260 | 686 | 400 |
| n-tetradecyl | 1150 | 651 | 400 |

B. Acylation of A-30912A Nucleus

A solution of A-30912A nucleus (400 mg., 0.5 mmole) and p-(n-decylsulfonyl)benzoic acid 2,4,5-trichlorophenyl ester (260 mg., 0.514 mmole) in dimethylformamide (50 ml.) is allowed to stir at room temperature for 18 hours. The reaction mixture is evaporated to dryness in vacuo, and the residue is extracted twice with diethyl ether and methylene chloride. The residue, dissolved in a minimum amount of an ethyl acetate-methanol mixture (3:2, v/v), is then applied to a silica gel column (50 ml.) and eluted with the same solvent mixture. The course of the chromatography is followed by TLC on silica gel (Merck) using ethyl acetate-methanol (3:2) as the solvent system. Fractions containing the desired product ($R_f \cong 0.6$) are combined, evaporated to dryness, and lyophilized. Weight of p-(n-decylsulfonyl)benzoyl derivative of A-30912A nucleus: 415 mg. Field desorption mass spectral analysis shows $(M^+ + 23) = 1128$. Analytical HPLC shows the product to be a single component.

Following the above procedure, other p-(alkylsulfonyl)benzoyl derivatives of A-30912A nucleus can be made as shown below:

| p-Alkylsulfonyl benzoyl derivative | Wt. of nucleus (mg) | Wt. of ester reactant (mg) | Wt. of product (mg) | $M^+[Na]^+$ |
|---|---|---|---|---|
| n-octyl | 400 | 69 | 83 | — |
| n-dodecyl | 400 | 267 | 335 | 1156 |
| n-tetradecyl | 400 | 281 | 322 | 1184 |

C. Preparation of p-(Alkylsulfinyl)benzoic Acid 2,4,5-Trichlorophenyl Ester

To a solution of 2,4,5-trichlorophenyl p-(n-octylthio)-benzoate (2.23 g, 5 mmole) in methylene chloride (50 ml) cooled in an ice bath is added dropwise a solution of m-chloroperbenzoic acid (1.39 g, 8 mmole, in 50 ml of methylene chloride). The solution is stirred at 5° C. for about 2 hours and then at room temperature for about 2 hours. After adding 2-3 drops of 20% $Na_2SO_3$ solution, the reaction mixture is washed once with 10% $NaHCO_3$ solution and twice with water. The organic layer is dried ($MgSO_4$) and concentrated under vacuum to give a residue which is crystallized from diethyl ether:petroleum ether (1:4) to give 1.7 g of product which is a mixture of the sulfinyl and the sulfonyl compounds.

D. Acylation of A-30912A Nucleus

A solution of A-30912A nucleus (800 mg, 1 mmole) in DMF (25 ml) is reacted with the product obtained in Sect. C (922 mg, 2 mmole) as described in Sect. B to give 952 mg of mixed product. This product is chromatographed over silica gel (100 g of 100–200 mesh), using an ethyl acetate:methanol (3:2) solvent system. The first fractions obtained from this column (554 mg) are rechromatographed over silica gel, using ethyl acetate to which increasing amounts of methanol are added as the eluting solvent. Fractions are combined on the basis of TLC results. After elution of the p-(n-octylsulfonyl)benzoyl derivative of A-30912A nucleus (58 mg), the p-(n-octylsulfinyl)benzoyl derivative of A-30912A nucleus is eluted to give 145 mg of product.

EXAMPLE 5

The following procedure illustrates the large-scale preparation of the compounds of Formula III. The specific compound prepared by the procedure given below is the compound of formula III wherein $R^1$ is p-(n-octyloxy)benzoyl.

A. Preparation of p-(n-Octyloxy)benzoic Acid

A solution of p-hydroxybenzoic acid (19.2 g., 150 mmole) in 10% aqueous sodium hydroxide (120 ml.) is added to DMSO (480 ml.) previously heated to 80° C. n-Octyl bromide (28.95 g., 150 mmole) is added dropwise to the solution. The reaction mixture is stirred for 4 hours at room temperature after which it is poured into ice water (1200 ml.). Conc. hydrochloric acid (30 ml.) is added, and the mixture is allowed to stand until precipitation is complete. The precipitate is collected, dried, and crystallized from acetonitrile-water. m.p. 97°–99° C.

Analysis for $C_{15}H_{22}O_3$: Calculated: C, 71.97; H, 8.86. Found: C, 71.72; H, 9.10.

B. Preparation of the 2,4,5-Trichlorophenyl Ester of p-(n-Octyloxy)benzoic Acid p-(n-Octyloxy)benzoic acid (6.18 g., 24.7 mmole), 2,4,5-trichlorophenol (5.39 g., 27.2 mmole) and N,N'-dicyclohexylcarbodiimide (4.94 g., 24.7 mM) are dissolved in methylene chloride (200 ml.). The mixture is stirred at room temperature for 18 hours and then is filtered. The filtrate is evaporated to give an oil, which is crystallized from $CH_3CN$—$H_2O$ to give the 2,4,5-trichlorophenyl ester of p-(n-octyloxy)benzoic acid.

NMR Analysis: $\delta 4.02$ (2H, t, J=3 Hz), $\delta 7.0$ (1H, d, J=4 Hz), 7.23 (s, 1H), 7.3 (s, 1H), 8.08 (d, 1H, J=4 Hz).

C. Acylation of A-30912A Nucleus

A-30912A nucleus (14.2 g., 17.8 mmole) and the 2,4,5-trichlorophenyl ester of p-(n-octyloxy)benzoic acid (15.32 g., 35.7 mmole) are dissolved in dimethylformamide (150 ml.). The solution is stirred at room temperature for 16–20 hours. Solvent is removed in vacuo, and the residue is washed twice with diethyl ether and twice with methylene chloride. The washes are discarded. The washed residue is dissolved in 25% ethyl acetate-methanol (80 ml.) and is purified by high performance liquid chromatography using a "Prep LC/System 500" unit (Waters Associates, Inc., Milford, Mass.) employing silica gel as the stationary phase. The column is eluted stepwise with 20% to 40% methanol-ethyl acetate solvent systems. The fractions are analyzed by TLC using silica gel (Merck) and ethyl acetate-methanol (3:2 v/v) as the solvent system. Fractions devoid of A-30912A nucleus are pooled and lyophilized to give the p-(n-octyloxy)benzoyl derivative of A-30912A nucleus. Yield: 7.13 g.; M+ +23: 1052 (by FDMS).

EXAMPLE 6

The antifungal activity of the compounds of Formula III can be demonstrated and elicited in vitro in standard disc-diffusion tests and agar dilution tests, and in vivo in standard tests in mice which assess effectiveness against a systemic fungal infection. The results of the antifungal testing of representative compounds of Formula III (Examples 3 and 4) are set forth in Tables 10, 11, 12, and 13.

Tables 10 and 11 give the results of the testing in vitro of the compounds of Examples 3 and 4 by agar-plate disc-diffusion methods. In Table 10 activity is measured by the size (diameter in mm) of the observed zone of inhibition of the microorganism produced by the test compound. In Table 11, activity is measured by the minimal inhibitory concentration (MIC) of the substance (μg/disc) required to inhibit growth of the test organism. Table 12 gives the results of the testing in vitro of the p-(n-octyloxy)benzoyl derivative of A30912A nucleus [Formula III, $R^1$ is p-(n-octyloxy)benzoyl] against five strains of *Candida albicans* by the agar dilution method. In Table 12 activity is measured by the minimal inhibitory concentration (MIC) of the substance (μg/ml) required to inhibit the test organism.

The results of in vivo tests to evaluate the effectiveness of the compounds of Examples 3 and 4 against an infection caused by *Candida albicans* A-26 in mice are given in Table 13, where activity is measured by the $ED_{50}$ value (the dose in mg/kg. required to cure 50% of the test animals). In a separate test, the results of which are also summarized in Table 13, activity is indicated by the lowest dose at which a significant anti-fungal effect is observed. In this test, groups of male albino mice (specific pathogen free), weighing 18 to 20 grams, are infected intravenously with *Candida albicans* A-26. The animals are X-irradiated 24 hours prior to infection at about 50 roentgens per minute for 8 minutes (400 total dose) to reduce immune responses to the infecting organism. At 0, 4, and 24 hours post infection each group of mice is given graded doses subcutaneously of the test compound as a suspension in 33% polyethylene glycol (PEG)-water. The day of death for each animal is recorded. Student's test statistical comparison of the average day of death is made between each group of infected-treated animals at a particular dosage level and 10 infected-untreated animals to determine if treatment significantly extends survival time.

Table 14 gives the results of the testing of the compounds of Example 3 and 4 for absorption after oral administration. In this test, mice are gavaged with a dose of 416 mg/kg of the test compound suspended in 33% PEG 400-water. At time intervals, blood samples are taken from the orbital sinus and are assayed for antibiotic activity as follows: A 7 mm. disc containing 20 μl of whole blood is placed on agar seeded with *Aspergillus montevidensis* A35137. After 40 hours incubation at 30° C. zones of inhibition from the blood samples are compared to a standard obtained from the test compound, and the amount of compound in the blood sample is calculated.

TABLE 10

Antifungal Activity By the Agar Plate Disc Diffusion Test

| Compound $R^1$ of Formula III | Size of Zone of Inhibition (mm)[a] | | | |
|---|---|---|---|---|
| | *Saccharomyces pastoranius* X-52 | *Neurospora crassa* 846 | *Trichophyton mentagraphytes* A-23 | *Candida albicans* A-26 |
| 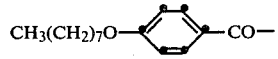 $CH_3(CH_2)_7O$—〈 〉—CO— | 18 | 23* | — | 28 |
|  $CH_3(CH_2)_{11}O$—〈 〉—CO— | 13 | — | — | 18 |
|  $CH_3(CH_2)_{13}O$—〈 〉—CO— | 13 | 24* | — | 19 |
|  $CH_3(CH_2)_{13}S$—〈 〉—CO— | 20 | 15 | 19* | 19 |
|  $CH_3(CH_2)_9SO_2$—〈 〉—CO— | 16 | 31 | 32 | 55 |
| 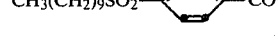 $CH_3(CH_2)_{11}SO_2$—〈 〉—CO— | — | 37 | 26 | 48 |
| 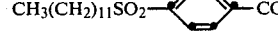 $CH_3(CH_2)_{13}SO_2$—〈 〉—CO— | 23 | 29 | 23 | 30 |

[a]Compounds were tested as suspension in methanol. The compounds were tested at a concentration of 1 mg/ml. by dipping a 7-mm disc into the suspension and placing it on the agar surface. Incubation: 24–48 hours at 25–37° C.
*Measurable zone of inhibition with regrowth of organism around disc.

TABLE 11
Antifungal Activity By the Agar Plate Disc Diffusion Test

| Compound R¹ of Formula III | MIC (μg/disc)[a] | |
|---|---|---|
| | Candida albicans A-26 | Trychophyton mentagrophyes #6* |
| $CH_3(CH_2)_7O$—⟨⟩—CO— | 0.156 | <0.039 |
| $CH_3(CH_2)_9O$—⟨⟩—CO— | 0.156 | <0.078 |
| $CH_3(CH_2)_{11}O$—⟨⟩—CO— | 2.5 | <0.039 |
| $CH_3(CH_2)_{13}O$—⟨⟩—CO— | 0.625 | <0.078 |
| $CH_3(CH_2)_7S$—⟨⟩—CO— | 0.312 | <0.039 |
| $CH_3(CH_2)_9S$—⟨⟩—CO— | 0.156 | 0.039 |
| $CH_3(CH_2)_{11}S$—⟨⟩—CO— | 2.5 | <0.039 |
| $CH_3(CH_2)_{13}S$—⟨⟩—CO— | 20.0 | <0.039 |
| $CH_3(CH_2)_7SO_2$—⟨⟩—CO— | 20 | 0.312 |
| $CH_3(CH_2)_9SO_2$—⟨⟩—CO— | 2.5 | 0.156 |
| $CH_3(CH_2)_{11}SO_2$—⟨⟩—CO— | 0.625 | 0.078 |
| $CH_3(CH_2)_{13}SO_2$—⟨⟩—CO— | 0.625 | 0.039 |
| $CH_3(CH_2)_7O$—⟨⟩—CO— | 10 | >40 |
| $CH_3(CH_2)_9O$—⟨⟩—CO— | 2.5 | >40 |
| $CH_3(CH_2)_{11}O$—⟨⟩—CO— | 2.5 | >40 |
| $CH_3(CH_2)_{13}O$—⟨⟩—CO— | 40 | 40 |
| $CH_3(CH_2)_5O$—⟨⟩—CO— | 2.5 | 0.312 |
| $CH_3(CH_2)_7(SO)$—⟨⟩—CO— | 5 | 1.25 |
| $CH_3(CH_2)_7$—⟨⟩—CO— | 0.625 | 0.156 |
| $CH_3(CH_2)_3O$—⟨⟩—$(CH_2)_2$—CO— | 20 | 1.25 |
| $CH_3(CH_2)_5O$—⟨⟩—$(CH_2)_2$—CO— | 0.625 | 0.156 |
| $CH_3(CH_2)_7O$—⟨⟩—$(CH_2)_2$—CO— | 0.078 | 0.156 |
| $CH_3(CH_2)_{11}O$—⟨⟩—$(CH_2)_2$—CO— | 0.312 | 0.156 |
| $CH_3(CH_2)_{10}$—⟨⟩—$(CH_2)_{11}$—CO— | 1.25 | 40 |

TABLE 11-continued

Antifungal Activity By the Agar Plate Disc Diffusion Test

| Compound R¹ of Formula III | MIC (μg/disc)[a] | |
|---|---|---|
| | Candida albicans A-26 | Trychophyton mentagrophyes #6* |
| $CH_3(CH_2)_5O$—⟨ ⟩—CH=CH—CO— | 1.25 | 0.156 |
| $CH_3(CH_2)_7O$—⟨ ⟩—CH=CH—CO— | 0.156 | 0.156 |
| $CH_3(CH_2)_7O$—⟨ ⟩—CH₂CO— | 5 | 80 |
| $CH_3(CH_2)_{11}O$—⟨ ⟩—CH₂CO— | 0.312 | 0.625 |
| $CH_3(CH_2)_4O$—⟨ ⟩—(CH₂)₂—CO— | 5 | 0.156 |
| $CH_3(CH_2)_6O$—⟨ ⟩—(CH₂)₂—CO— | 0.625 | 0.156 |
| $CH_3(CH_2)_7O$—⟨ ⟩—O—CH₂—CO— | 0.312 | 80 |
| $CH_3(CH_2)_9O$—⟨ ⟩—O—CH₂CO— | 0.156 | <0.156 |
| $CH_3(CH_2)_7O$—⟨N⟩—CO— | 80 | 2.5 |

[a]Compounds were suspended in 0.1M sodium borate solution, pH 7.5. The compounds were tested at 20 μg/disc at top level and at two-fold dilutions until end points were reached. Incubation: 24 hours; 30° C.
*Measurable zones of inhibition with regrowth of organism around disc.

TABLE 12

In vitro activity of derivatives of A-30912A nucleus against 5 strains of Candida albicans

| Compound R¹ of Formula III | MIC (μg/ml.) | | | | |
|---|---|---|---|---|---|
| | A-26 | SBH16 | SBH31 | SBH28 | SBH29 |
| $CH_3(CH_2)_8O$—⟨ ⟩—CO— | 0.312 | 0.312 | 0.312 | 0.312 | 0.312 |
| $CH_3(CH_2)_{11}S$—⟨ ⟩—CO— | 0.625 | 0.625 | 0.625 | 0.625 | 0.625 |
| $CH_3(CH_2)_{13}S$—⟨ ⟩—CO— | 2.5 | 2.5 | 2.5 | 2.5 | 2.5 |

TABLE 13

Therapeutic Activity Against Candida Albicans A-26 in Mice*

| Compound R¹ of Formula III | ED₅₀ (mg/kg)** | Lowest Active Dose (mg/kg) |
|---|---|---|
| $CH_3(CH_2)_7O$—⟨ ⟩—CO— | 13<br>22.2 | 10<br><12.5 |
| $CH_3(CH_2)_9O$—⟨ ⟩—CO— | 8 | 5 |
| $CH_3(CH_2)_{11}O$—⟨ ⟩—CO— | <5<br>3.9 | ≦5<br>2.5 |
| $CH_3(CH_2)_{13}O$—⟨ ⟩—CO— | 3 | 5 |
| $CH_3(CH_2)_7S$—⟨ ⟩—CO— | 37.4 | 10 |
| $CH_3(CH_2)_9S$—⟨ ⟩—CO— | 28 | 20 |
| $CH_3(CH_2)_{11}S$—⟨ ⟩—CO— | 2 | <1.25 |
| $CH_3(CH_2)_{13}S$—⟨ ⟩—CO— | 20 | 2.5 |
| $CH_3(CH_2)_7SO_2$—⟨ ⟩—CO— | 57 | — |
| $CH_3(CH_2)_9SO_2$—⟨ ⟩—CO— | 57 | — |

TABLE 13-continued
Therapeutic Activity Against *Candida Albicans* A-26 in Mice*

| Compound $R^1$ of Formula III | $ED_{50}$ (mg/kg)** | Lowest Active Dose (mg/kg) |
|---|---|---|
| $CH_3(CH_2)_{11}SO_2$—⟨furan⟩—CO— | 53 | 20 |
| $CH_3(CH_2)_{13}SO_2$—⟨furan⟩—CO— | 11 | 5 |
| $CH_3(CH_2)_7O$—⟨furan⟩—CO— | >50 | 40 |
| $CH_3(CH_2)_9O$—⟨furan⟩—CO— | >50 | >40 |
| $CH_3(CH_2)_{11}O$—⟨furan⟩—CO— | >50 | >40 |
| $CH_3(CH_2)_{13}O$—⟨furan⟩—CO— | >50 | >40 |
| $CH_3(CH_2)_5O$—⟨furan⟩—CO— | 28 | 20 |
| $CH_3(CH_2)_7(SO)$—⟨furan⟩—CO— | 56.6 | >40 |
| $CH_3(CH_2)_7$—⟨furan⟩—CO— | 30 | 40 |
| $CH_3(CH_2)_3O$—⟨furan⟩—$(CH_2)_2$—CO— | >40 | 40 |
| $CH_3(CH_2)_5O$—⟨furan⟩—$(CH_2)_2$—CO— | 9.2 | 5 |
| $CH_3(CH_2)_7O$—⟨furan⟩—$(CH_2)_2$—CO— | 4.5 | |
| $CH_3(CH_2)_{11}O$—⟨furan⟩—$(CH_2)_2$—CO— | 4.5 | |
| $CH_3(CH_2)_{10}$—⟨furan⟩—$(CH_2)_{11}$—CO— | >40 | 20 |
| $CH_3(CH_2)_5O$—⟨furan⟩—CH=CH—CO— | 21.8 | 5 |
| $CH_3(CH_2)_7O$—⟨furan⟩—CH=CH—CO— | 3.75 | 5 |
| $CH_3(CH_2)_7O$—⟨furan⟩—$CH_2CO$— | >40 | 10 |
| $CH_3(CH_2)_{11}O$—⟨furan⟩—$CH_2CO$— | 8.4 | 10 |
| $CH_3(CH_2)_7O$—⟨furan⟩—O—$CH_2$—CO— | 16.8 | 10 |
| $CH_3(CH_2)_{11}$—O—⟨furan⟩—$CH_2CO$— | 7.4 | 20 |

*Dosage Schedules: A. = 40, 20, 15 and 10 mg/kg; Dosages given 0, 4, and 24 hours post injection as suspension of test compound in 30% PEG-H₂O. Number of mice receiving test compounds at each dosage level: 6 mice per group. Number of mice in control (untreated) group: 10 mice per group.
**As measured by increase in survival time of treated animals versus control, calculated by method of Reed v Mueuch, American J. Hygiene, 27, 493 (1938).

TABLE 14
Blood Levels After Oral Administration In Mice

| Compound $R^1$ of Formula III | Highest Blood Level Determined During a 4-Hour Time Interval (μg/ml.) |
|---|---|
| $CH_3(CH_2)_7O$—⟨furan⟩—CO— | 23 |
| $CH_3(CH_2)_9O$—⟨furan⟩—CO— | <0.1 |
| $CH_3(CH_2)_{11}O$—⟨furan⟩—CO— | 5 |
| $CH_3(CH_2)_{13}O$—⟨furan⟩—CO— | 5 |
| $CH_3(CH_2)_7S$—⟨furan⟩—CO— | <0.1 |
| $CH_3(CH_2)_9S$—⟨furan⟩—CO— | 5 |
| $CH_3(CH_2)_{11}S$—⟨furan⟩—CO— | 30 |
| $CH_3(CH_2)_{13}S$—⟨furan⟩—CO— | 230 |

*Test compound administered at dose of 416 mg/kg by gavage as suspension of compound in 33% PEG 400-H₂O. Antifungal activity determined by bioassay vs. *Aspergillus montevidensis* A-35137.

EXAMPLE 7
Preparation of A-30912A Nucleus

A. Fermentation of *Actinoplanes utahensis* NRRL 12052

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Baby oatmeal | 60.0 g |
| Yeast | 2.5 g |
| K₂HPO₄ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.

*Czapek's mineral stock has the following composition:

| Ingredient | Amount |
|---|---|
| FeSO₄ . 7H₂O (dissolved in 2 ml conc HCl) | 2 g |
| KCl | 100 g |
| MgSO₄ . 7H₂O | 100 g |
| Deionized water | q.s. to 1 liter |

| MEDIUM B | |
|---|---|
| Ingredient | Amount |
| Potato dextrin | 5.0 g |
| Yeast extract | 0.5 g |
| Enzymatic hydrolysate of casein* | 3.0 g |
| Beef extract | 0.5 g |
| Dextrose | 12.5 g |
| Corn starch | 5.0 g |
| Meat peptone | 5.0 g |
| Blackstrap molasses | 2.5 g |
| MgSO₄ . 7H₂O | 0.25 g |

-continued

| | |
|---|---|
| CaCO$_3$ | 1.0 g |
| Czapek's mineral stock | 2.0 ml |
| Agar | 20.0 g |
| Deionized water | q.s. to 1 liter |

*N-Z-Amine A, Humko Sheffield Chemical, Lyndhurst, N.J.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Baby oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water | q.s to 1 liter | adjust to pH 7.4 with NaOH; after autoclaving, pH is about 6.8.
*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen, *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| KH$_2$PO$_4$ | 0.5 |
| K$_2$HPO$_4$ | 1.2 |
| MgSO$_4$ . 7H$_2$O | 0.25 |
| Tap water | q.s to 1 liter |

The pH of the medium is about 6.9 after sterilization by autoclaving at 121° C. for 45 minutes at about 16–18 psi.

| MEDIUM II | |
|---|---|
| Ingredient | Amount (g/L) |
| Sucrose | 30.0 |
| Peptone | 5.0 |
| K$_2$HPO$_4$ | 1.0 |
| KCl | 0.5 |
| MgSO$_4$ . 7H$_2$O | 0.5 |
| FeSO$_4$ . 7H$_2$O | 0.002 |
| Deionized water | q.s. to 1 liter |

Adjust to pH 7.0 with HCl; after autoclaving, pH is about 7.0.

| MEDIUM III | |
|---|---|
| Ingredient | Amount (g/L) |
| Glucose | 20.0 |
| NH$_4$Cl | 3.0 |
| Na$_2$SO$_4$ | 2.0 |
| ZnCl$_2$ | 0.019 |
| MgCl$_2$ . 6H$_2$O | 0.304 |
| FeCl$_3$ . 6H$_2$O | 0.062 |
| MnCl$_2$ . 4H$_2$O | 0.035 |
| CuCl$_2$ . 2H$_2$O | 0.005 |
| CaCO$_3$ | 6.0 |
| KH$_2$PO$_4$* | 0.67 |
| Tap water | q.s to 1 liter |

Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level above 30% of air saturation at atmospheric pressure.

B. Deacylation of A-30912A

A fermentation of *A. utahensis* is carried out as described in Sect. A, using slant medium A and production medium I and incubating the production medium for about 42 hours. A-30912 factor A (340 g. of crude substrate which contained about 19.7 g. of A-30912 factor A, dissolved in 1.5 L ethanol) is added to the fermentation medium. Deacylation of A-30912 factor A is monitored by assay against *Candida albicans*. The fermentation is allowed to continue until deacylation is complete as indicated by disappearance of activity vs. *C. albicans*.

C. Isolation of A-30912A Nucleus

Whole fermentation broth (100 liters), obtained as described in Sect. B and containing nucleus from about 20 g of A-30912 factor A, is filtered. The mycelial cake is discarded. The clear filtrate thus obtained (about 93 liters) is passed through a column containing 4.5 liters of HP-20 resin (DIAION High Porous Polymer, HP-Series, Mitsubishi Chemical Industries Limited, Tokyo, Japan) at a rate of 200 ml/minute. The effluent thus obtained is discarded. The column is then washed with up to eight column volumes of deionized water at pH 6.5–7.5 to remove residual filtered broth. This wash water is discarded. The column is then eluted with a water:methanol (7:3) solution (85 liters) at a rate of 200–300 ml/minute.

Elution is monitored using the following procedure: Two aliquots are taken from each eluted fraction. One of the aliquots is concentrated to a small volume and is treated with an acid chloride such as myristoyl chloride. This product and the other (untreated) aliquot are assayed for activity against *Candida albicans*. If the untreated aliquot does not have activity and the acylated aliquot does have activity, the fraction contains A-30912A nucleus. The eluate containing the A-30912A nucleus is concentrated under vacuum to a small volume and lyophilized to give approximately 97 grams of crude nucleus.

D. Purification of A-30912A Nucleus by Reversed-Phase Liquid Chromatography

Crude A-30912A nucleus (25 grams), obtained as described in Section C, is dissolved in 300 ml of water:acetonitrile:acetic acid:pyridine (96:2:1:1). This solution is chromatographed on a 4-liter stainless-steel column (8 cm × 80 cm) filled with Lichroprep RP-18, particle size 25–40 microns (MC/B Manufacturing Chemists, Inc. E/M, Cincinnati, OH). The column is part of a Chromatospac Prep 100 unit (Jobin Yvon, 16–18 Rue du Canal 91160 Longjumeau, France). The column is operated at a pressure of 90–100 psi, giving a flow rate of about 60 ml/minute, using the same solvent. Separation is monitored at 280 nm using a UV monitor (ISCO Absorption Monitor Model UA-5, Instrumention Specialties Co., 4700 Superior Ave., Lincoln, Nebr. 68504) with an optical unit (ISCO Type 6). Fractions having a volume of about 500 ml are collected each minute.

On the basis of absorption at 280 nm, fractions containing A-30912A nucleus are combined, evaporated under vacuum and lyophilized to give 2.6 grams of nucleus. The amount of solvent required to complete this chromatographic separation process varies from 7–8 liters.

A30912A nucleus has the following characteristics:
(a) Empirical formula: $C_{34}H_{51}N_7O_{15}$.
(b) Molecular weight: 779.
(c) Soluble in water, dimethylformamide, dimethyl sulfoxide, and methanol; insoluble in chloroform, toluene, and diethyl ether.
(d) Infrared absorption spectrum (KBr disc.

Shows absorption maxima at: 3340 broad (OH, H-bonded); 2970, 2930, and 2890 (CH); 1625 (several carbonyls C=O); 1510–1550; 1430–1450 (CH wag); 1310–1340; 1230–1260; 1080; 835, 650 broad, and 550 broad cm$^{-1}$.

(e) Electrometric titration in 66% aqueous dimethylformamide indicates the presence of a titratable group with a $pK_a$ value of about 7.35 (initial pH 7.32).
(f) HPLC retention time (K'):11.52 min. under following conditions.
Column: 4×300 mm
Packing: silica gel/$C_{18}$
Solvent: ammonium acetate:acetonitrile:water (1:2:97)
Flow Rate: 3 ml/min
Pressure: 2500 psi
Detector: variable wavelength UV at 230 nm
Sensitivity: 0–0.4 A.U.F.S.

EXAMPLE 8

A-30912A nucleus is prepared and purified by the method of Example 7 except that tetrahydro-A-30912A is used as the substrate in Sect. B.

EXAMPLE 9

A-30912A nucleus is prepared and purified by the method of Example 7 except that aculeacin A is used as the substrate in Sect. B.

EXAMPLE 10

Preparation of the A-42355 Antibiotic Complex

A. Shake-Flask Fermentation

A culture of *Aspergillus nidulans* var. roseus NRRL 11440 is prepared and maintained on an agar slant prepared with sodium having the following composition.

| Ingredient | Amount |
|---|---|
| Glucose | 5 g |
| Yeast extract | 2 g |
| CaCO$_3$ | 3 g |
| Vegetable juice* | 200 ml |
| Agar** | 20 g |
| Deionized water | q.s to 1 liter |

(initial pH 6.1)
*V-8 Juice, Campbell Soup Co., Camden, N.J.
**Meer Corp.

The slant is inoculated with *Aspergillus nidulans* var. roseus NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculate 55 ml of vegetative medium in a 250-ml flask. The vegetative medium has the following composition:

| Ingredient | Amount |
|---|---|
| Sucrose | 25 g |
| Blackstrap molasses | 36 g |
| Corn-steep liquor | 6 g |
| Malt extract | 10 g |
| K$_2$HPO$_4$ | 2 g |
| Enzymatic hydrolysate of casein* | 10 g |
| Tap water | 1100 ml |

(initial pH 6.5–6.7)
*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-type vegetative medium. Alternatively, it can be stored for later use by maintaining the culture in the vapor phase of liquid nitrogen. The culture is prepared for such storage in multiple small vials as follows: The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

| MEDIUM IV | |
| --- | --- |
| Ingredient | Amount |
| $ZnSO_4 \cdot 7H_2O$ | 0.00455 g/L |
| Soluble meat peptone* | 30.5 g/L |
| Soybean meal | 15.5 g/L |
| Tapioca dextrin** | 2.0 g/L |
| Blackstrap molasses | 10.5 g/L |
| Enzymatic hydrolysate of casein*** | 8.5 g/L |
| $Na_2HPO_4$ | 4.5 g/L |
| $MgSO_4 \cdot 7H_2O$ | 5.5 g/L |
| $FeSO_4 \cdot 7H_2O$ | 0.1 g/L |
| Cottonseed oil | 40.0 ml |
| (Antifoam)**** | 1.0 ml |
| Tap water | 1000.0 ml |

(initial pH 6.8–7.0)
*O.M. Peptone, Amber Laboratories, Juneau, Wisc.
**Stadex 11, A.E. Staley Co., Decatur, Ill.
***N-Z-Amine A, Humko Sheffield Chemical, Lyndhurst, N.J.
****P2000, Dow Corning, Midland, Michigan

| MEDIUM V | |
| --- | --- |
| Ingredient | Amount |
| Glucose | 2.5% |
| Starch | 1.0% |
| Soluble meat peptone* | 1.0% |
| Blackstrap molasses | 1.0% |
| $CaCO_3$ | 0.2% |
| $MgSO_4 \cdot 7H_2O$ | 0.05% |
| Enzymatic hydrolysate of casein** | 0.4% |
| (Antifoam)*** | 0.02% |
| Tap water | q.s. to volume |

*O.M. Peptone
**N-Z-Amine A
***Antifoam "A" Dow Corning the inoculated production medium is allowed to ferment in a 165-liter fermentation tank at a temperature of 25° C. for about 7 days. The fermentation medium is aerated with sterile air, maintaining the dissolved oxygen level above approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount |
| --- | --- |
| Sucrose | 25 g |
| Blackstrap molasses | 25 g |
| Corn-steep liquor | 6 g |
| Enzymatic hydrolysate of casein* | 10 g |
| Malt extract | 10 g |
| $K_2HPO_4$ | 2 g |
| Tap water | 1000 ml |

(initial pH 6.1)
*N-Z-Case

EXAMPLE 11

Separation of the A-42355 Antibiotic Complex

Whole fermentation broth (4127 liters), obtained by the method described in Example 10 using production medium V, is stirred thoroughly with methanol (4280 liters) for one hour and then is filtered, using a filter aid (Hyflo Super-cel, a diatomaceous earth, Johns-Manville Products Corp.). The pH of the filtrate is adjusted to pH 4.0 by the addition of 5 N HCl. The acidified filtrate is extracted twice with equal volumes of chloroform. The chloroform extracts are combined and concentrated under vacuum to a volume of about 20 liters. This concentrate is added to about 200 liters of diethyl ether to precipitate the A-42355 complex. The precipitate is separated by filtration to give 2775 g of the A-42355 complex as a gray-white powder.

EXAMPLE 12

Isolation of A-30912 Factor A

The co-pending application of Karl H. Michel entitled RECOVERY PROCESS FOR A-30912 ANTIBIOTICS, Ser. No. 103,014, filed Dec. 13, 1979, describes the reversed-phase high performance, low pressure liquid chromatography (HPLPLC) using silica gel/$C_{18}$ adsorbent as a preferred method for the final purification of A-30912 factor A.

A-42355 antibiotic complex (1 g), prepared as described in Example 11, is dissolved in 7 ml of methanol:water:acetonitrile (7:2:1). This solution is filtered and introduced onto a 3.7-cm I.D.×35-cm glass column [Michel-Miller High Performance Low Pressure (HPLPLC) Chromatography Column, Ace Glass Incorporated, Vineland, NJ 08360] packed with LP-1/$C_{18}$ silica gel reversed-phase resin (10–20 microns), prepared as described in Example 13, through a loop with the aid of a valve system. The column is packed in methanol:water:acetonitrile (7:2:1) by the slurry-packing procedure described in Example 14. An F.M.I. pump with valveless piston design (maximum flow 19.5 ml/minute) is used to move the solvent through the column at a flow rate of 9 ml/minute at ca. 100 psi, collecting fractions every minute. Elution of the antibiotic is monitored at 280 nm by using a UV monitor (ISCO Model UA-5, Instrument Specialist Co., 4700 Superior Ave., Lincoln, Nebr. 68504) with an optical unit (ISCO Type 6).

The individual A-30912 factors can be identified by the use of thin-layer chromatography (TLC). The $R_f$ values of A-30912 factors A-G, using silica gel (Merck, Darmstadt) TLC, a benzene:methanol (7:3) solvent system, and *Candida albicans* bioautography are given in Table 15.

TABLE 15

| A-30912 Factor | $R_f$ Value |
|---|---|
| A | 0.35 |
| B | 0.45 |
| C | 0.54 |
| D | 0.59 |
| E | 0.27 |
| F | 0.18 |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table 16.

TABLE 16

| A-30912 Factor | $R_f$ Values - Solvent Systems | | | |
|---|---|---|---|---|
| | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a ethyl acetate:methanol (3:2)
b ethyl acetate:methanol (7:3)
c acetonitrile:water (95:5)
d ethyl acetate:ethanol:acetic acid (40:60:0.25)

A-30912 factors A, B, D and H can also be indentified by analytical HPLPLC using the following conditions:

| Column: | glass, 0.8 × 15.0 cm |
|---|---|
| Packing: | Nucleosil ® 10-$C_{18}$ (Machery-Nagel and Company); packed using slurry-packing procedure of Example 8 |
| Solvent: | methanol:water:acetonitrile (7:2:1) |
| Sample Volume: | 8 mcl |
| Sample Size: | 8 mcg |
| Column Temperature: | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |
| Injection: | loop injection |

The approximate retention times for A-30912 factors A, B, D, and H under these conditions are summarized in Table 17.

TABLE 17

| A-30912 Factor | Retention Time (seconds) |
|---|---|
| A | 792 |
| B | 870 |
| H | 990 |
| D | 1,140 |

EXAMPLE 13

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16-20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16-20 hours).

EXAMPLE 14

Slurry Packing Procedure for Michel-Miller Columns

General Information

This procedure is employed for packing reversed phase silica gel $C_{18}$ resin, such as that described in Example 13.

Generally, a pressure of less than 200 psi and flow rates between 5-40 ml/minute are required for this slurry packing technique; this is dependent on column volume and size. Packing pressure should exceed the pressure used during actual separation by 30-50 psi; this will assure no further compression of the adsorbent during separation runs.

A sudden decrease in pressure may cause cracks or channels to form in the packing material, which would greatly reduce column efficiency. Therefore, it is important to let the pressure drop slowly to zero whenever the pump is turned off.

The approximate volume of columns (Ace Glass Cat. No., unpacked) are No. 5795-04, 12 ml; No. 5795-10, 110 ml; No. 5795-16, 300 ml; No. 5795-24, 635 ml; and No. 5796-34, 34 ml.

The time required to pack a glass column will vary from minutes to several hours depending on column size and the experience of the scientist.

Example

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant.

5. Slurry the resin with sufficient solvent to fill reservoir column. Pour swiftly into reservoir. The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure. Always allow pressure to decrease slowly after turning off pump--this will prevent formation of any cracks or channels in the packing material.

10. Relieve pressure and disconnect precolumn carefully. With small spatula remove a few mm (2-4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 15

Preparation of Tetrahydro-A-30912A

A-30912 factor A is dissolved in ethanol. $PtO_2$ in absolute ethanol is reduced to form Pt, which in turn is used to reduce the A-30912 factor A catalytically, using hydrogenation under positive pressure until the reaction is complete (about 2–3 hours). The reaction mixture is filtered and concentrated under vacuum. The residue is dissolved in a small amount of tert-butanol and lyophilized to give tetrahydro-A-30912A.

What is claimed is:

1. A compound of the formula:

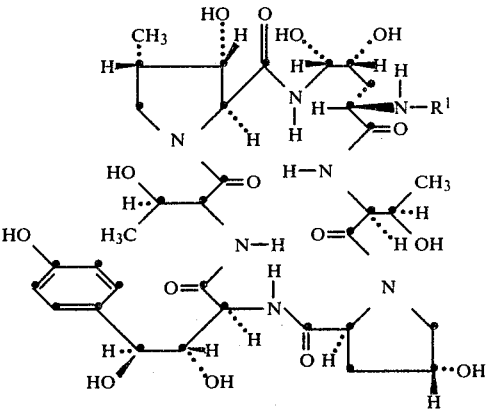

wherein $R^1$ is a group of the formula:

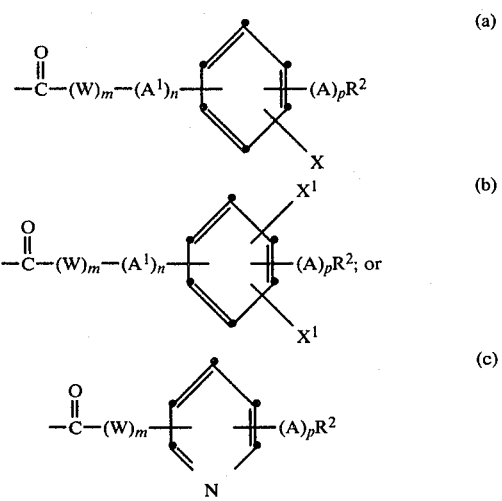

wherein A is divalent oxygen, sulfur, sulfinyl, or sulfonyl; $A^1$ is divalent oxygen, sulfur, sulfinyl, sulfonyl or —NH—; X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl or $C_1$–$C_3$ alkylcarbamyl; $X^1$ is chloro, bromo or iodo; $R^2$ is hydrogen $C_1$–$C_{18}$ alkyl or $C_2$–$C_{18}$ alkenyl; W is $C_1$–$C_{10}$ alkylene or $C_2$–$C_{10}$ alkenylene; m, n and p are 0 or 1, but if m=0, n must=0; provided: that the sum of the carbon atoms in the $R^2$ and W groups must be greater than 4 but cannot exceed 21; that when X is mercapto, A and $A^1$ cannot be sulfinyl or sulfonyl and that when A and $A^1$ are sulfinyl or sulfonyl, they must be in equal oxidation states.

2. A compound of claim 1 wherein $R^1$ is a substituted benzoyl group of the formula:

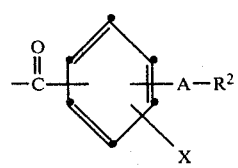

wherein A is divalent oxygen, sulfur, sulfinyl, or sulfonyl, X is hydrogen, chloro, bromo, iodo, nitro, $C_1$–$C_3$alkyl, hydroxy, $C_1$–$C_3$alkoxy, mercapto, $C_1$–$C_3$alkylthio, carbamyl, or $C_1$–$C_3$alkylcarbamyl; and $R^2$ is $C_5$–$C_{18}$alkyl or $C_5$–$C_{18}$alkenyl.

3. A compound as defined in claim 1 or 2 wherein A is oxygen.

4. A compound as defined in claim 3 wherein X is hydrogen and $R^2$ is straight chain $C_5$–$C_{18}$alkyl.

5. The compound as defined in claim 2 wherein $R^1$ is p-(n-octyloxy)benzoyl.

6. The compound as defined in claim 2 wherein $R^1$ is p-(n-decyloxy)benzoyl.

7. The compound as defined in claim 2 wherein $R^1$ is p-(n-dodecyloxy)benzoyl.

8. The compound as defined in claim 2 wherein $R^1$ is p-(n-tetradecyloxy)benzoyl.

9. The compound as defined in claim 2 wherein $R^1$ is p-(n-hexyloxy)benzoyl.

10. A compound as defined in claim 1 or 2 wherein A is sulfur.

11. A compound as defined in claim 10 wherein X is hydrogen and $R^2$ is straight chain $C_5$–$C_{18}$alkyl.

12. The compound as defined in claim 2 wherein $R^1$ is p-(n-octylthio)benzoyl.

13. The compound as defined in claim 2 wherein $R^1$ is p-(n-decylthio)benzoyl.

14. The compound as defined in claim 2 wherein $R^1$ is p-(n-dodecylthio)benzoyl.

15. The compound as defined in claim 2 wherein $R^1$ is p-(n-tetradecylthio)benzoyl.

16. A compound as defined in claim 1 or 2 wherein A is sulfonyl.

17. A compound as defined in claim 16 wherein X is hydrogen and $R^2$ is straight chain $C_5$–$C_{18}$ alkyl.

18. A compound as defined in claim 2 wherein $R^1$ is p-(n-octylsulfonyl)benzoyl.

19. A compound as defined in claim 2 wherein $R^1$ is p-(n-decylsulfonyl)benzoyl.

20. A compound as defined in claim 2 wherein $R^1$ is p-(n-dodecylsulfonyl)benzoyl.

21. A compound as defined in claim 2 wherein $R^1$ is p-(n-tetradecylsulfonyl)benzoyl.

22. A compound of claim 1 wherein $R^1$ is formula (a), X is hydrogen, and m, n and p are zero.

23. The compound of claim 22 wherein $R^1$ is p-(n-octyl)benzoyl.

24. A compound of claim 1 wherein $R^1$ is formula (a), X is hydrogen, A is oxygen, and n is zero.

25. The compound of claim 24 wherein $R^1$ is 3-[p-(n-hexyloxy)phenyl]propanoyl.

26. The compound of claim 24 wherein $R^1$ is 3-[p-(n-octyloxy)phenyl]propanoyl.

27. The compound of claim 24 wherein $R^1$ is 3-[p-(n-dodecyloxy)phenyl]propanoyl.

28. The compound of claim 24 wherein $R^1$ is p-(n-hexyloxy)cinnamoyl.

29. The compound of claim 24 wherein $R^1$ is p-(n-octyloxy)cinnamoyl.

30. The compound of claim 24 wherein $R^1$ is [p-(n-octyloxy)phenyl]acetyl.

31. The compound of claim 24 wherein $R^1$ is [p-(n-dodecyloxy)phenyl]acetyl.

32. The compound of claim 24 wherein $R^1$ is 3-[p-(n-pentyloxy)phenyl]propanoyl.

33. The compound of claim 24 wherein $R^1$ is 3-[p-(n-heptyloxy)phenyl]propanoyl.

34. A compound of claim 1 wherein $R^1$ is formula (a), X is hydrogen, and both A and $A^1$ are oxygen.

35. The compound of claim 34 wherein $R^1$ is p-(n-octyloxy)phenoxyacetyl.

36. The compound of claim 34 wherein $R^1$ is p-(n-decyloxy)phenoxyacetyl.

37. A compound of claim 1 wherein $R^1$ is formula (c).

38. The compound of claim 37 wherein $R^1$ is 6-(n-octyloxy)nicotinoyl.

39. The compound of claim 37 wherein $R^1$ is 6-(n-dodecyloxy)nicotinoyl.

40. The compound of claim 24 wherein $R^1$ is p-(n-decyloxy)cinnamoyl.

* * * * *

UNITED STATES PATENT AND TRADEMARK OFFICE
CERTIFICATE OF CORRECTION

PATENT NO. : 4,293,489

DATED : October 6, 1981

INVENTOR(S) : Manuel Debono

It is certified that error appears in the above—identified patent and that said Letters Patent is hereby corrected as shown below:

Column 40, lines 10-12, claim 1, that portion of the structural formula reading

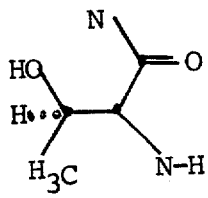

should read

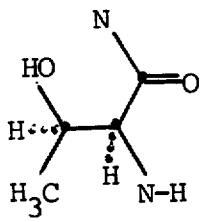

Column 40, line 47, "hydrogen $C_1$-$C_{18}$" should read -- hydrogen, $C_1$-$C_{18}$ --.

UNITED STATES PATENT AND TRADEMARK OFFICE
CERTIFICATE OF CORRECTION

PATENT NO. : 4,293,489

Page 2 of 2

DATED : October 6, 1981

INVENTOR(S) : Manuel Debono

It is certified that error appears in the above—identified patent and that said Letters Patent is hereby corrected as shown below:

Column 42, line 3, "$R^1$ isformula" should read -- $R^1$ is formula --.

Signed and Sealed this

Twenty-second Day of March 1983

[SEAL]

Attest:

GERALD J. MOSSINGHOFF

Attesting Officer

Commissioner of Patents and Trademarks